(12) United States Patent
Lee et al.

(10) Patent No.: US 10,806,766 B2
(45) Date of Patent: Oct. 20, 2020

(54) METHOD FOR TREATING, PREVENTING, OR ALLEVIATING OSTEOPOROSIS

(71) Applicant: LG HOUSEHOLD & HEALTH CARE LTD., Seoul (KR)

(72) Inventors: Youn Jung Lee, Daejeon (KR); Ho Song Cho, Daejeon (KR); Won Kyung Lee, Daejeon (KR); Soon Ran Song, Daejeon (KR); Sang Hwa Lee, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 16/520,969

(22) Filed: Jul. 24, 2019

(65) Prior Publication Data
US 2019/0343910 A1 Nov. 14, 2019

Related U.S. Application Data

(62) Division of application No. 15/697,137, filed on Sep. 6, 2017, now Pat. No. 10,406,190.

(51) Int. Cl.
*A61K 36/488* (2006.01)
*A61K 36/752* (2006.01)

(52) U.S. Cl.
CPC .......... *A61K 36/488* (2013.01); *A61K 36/752* (2013.01)

(58) Field of Classification Search
None
See application file for complete search history.

(56) References Cited

U.S. PATENT DOCUMENTS

| 9,974,822 | B2 | 5/2018 | Park et al. | |
| 2015/0265555 | A1* | 9/2015 | Baron | A61K 9/2054 514/217.01 |
| 2016/0039864 | A1* | 2/2016 | Prakash | A23L 27/36 426/72 |
| 2016/0206677 | A9 | 7/2016 | Cheung | |
| 2017/0258728 | A1* | 9/2017 | Yoshida | A61K 47/38 |
| 2018/0353407 | A1 | 12/2018 | Santhanam et al. | |
| 2019/0321299 | A1* | 10/2019 | Li | A61K 9/2072 |

FOREIGN PATENT DOCUMENTS

| CN | 101040646 | A | 9/2007 |
| CN | 101239092 | A | 8/2008 |
| CN | 103519175 | B | 8/2015 |
| CN | 107034118 | A | 8/2017 |
| JP | 2009 126853 | * | 9/2009 |
| KR | 10-2003-0031418 | A | 4/2003 |
| KR | 2003 031418 | * | 4/2003 |
| KR | 10-0851783 | B1 | 8/2008 |
| KR | 10-2015-0045036 | A | 4/2015 |

OTHER PUBLICATIONS

Cho et al, "The effects of Pueraria thomsonii flower extract on estrogenic activity, osteoblast differentiation and osteoclast formation in vitro," Maturitas, vol. 100, 2017, pp. 189, (Total p. 1).
Han N. et al., "Improvement Effects of a Mixed Extract of Flowers of Pueraria thomsonii Benth . . . ", Biomedicine & Pharmacotherapy, vol. 103, pp. 524-530, 2018.
Kim, J. et al., "Anti-Endometriotic Effects of Pueraria Flower Extract in Human Endometriotic Cells and Mice", Nutrients 9(3)212, pp. 1-14, Mar. 2017.
Shin, Ji-eun et al., "Estrogenic Effect of Main Components Kakkalide and Tectoridin of Puerariae Flos and Their Metabolites", Biol. Pharm. Bull., vol. 29, No. 6, 2006, pp. 1202-1206.

* cited by examiner

*Primary Examiner* — Ralph J Gitomer
(74) *Attorney, Agent, or Firm* — Birch, Stewart, Kolasch & Birch, LLP (57) ABSTRACT

The present invention relates to a composition for alleviating, preventing, or treating menopausal symptoms and/or osteoporosis. The composition of the present invention is rapidly effective in preventing or alleviating menopausal symptoms, and thus may be usefully used in conventional hormone replacement therapies (HRTs) used to prevent or alleviate menopausal symptoms. In addition, the composition of the present invention has no toxicity, can be used as food due to few side effects, and is safe, unlike conventional therapeutic agents for menopausal symptoms, and thus may be more effectively used as compared to conventional therapeutic agents for menopausal symptoms.

8 Claims, 2 Drawing Sheets

METHOD FOR TREATING, PREVENTING, OR ALLEVIATING OSTEOPOROSIS

CROSS REFERENCE TO RELATED APPLICATION

This application is a Divisional of U.S. application Ser. No. 15/697,137, filed on Sep. 6, 2017, which is hereby expressly incorporated by reference into the present application.

BACKGROUND

1. Field of the Invention

The present invention relates to a composition for preventing, alleviating, or treating female menopausal symptoms and/or osteoporosis which includes a mixed Puerariae Flos extract.

2. Discussion of Related Art

Women's menopause is a phenomenon of menstrual cessation that occurs when a genetically determined ovarian function of about 50 years after birth has reached the end of its life. This means loss of reproductive capacity and is not a morbid phenomenon, but is a physiological change. Currently, the average life expectancy of Korean women is 81.2 years, and, assuming that the average menopausal age of Korean women prescribed by the Korean Association of Obstetricians and Gynecologists is 50 years, this means that about one third or more of women's lives continue with depleted female hormones.

Due to the imbalance and reduction of female hormone secretion by menopause, changes occur throughout the whole body including the vascular system, the musculoskeletal system, the genitourinary system, the cranial nerve, and the like. That is, a variety of diseases and symptoms, for example, vascular mobility and psychological symptoms such as facial flushing, night sweating, sleeping disorders, fatigue, depression, anxiety, concentration disorders, and memory impairment; dyspareunia and urinary frequency due to urogenital atrophy; loss of skin elasticity and mastoptosis due to collagen reduction; cardiovascular and musculoskeletal symptoms; dementia; and the like co-occur. It is reported that 89% of women who have experienced natural menopause experience at least one menopausal symptom, and frequently experience menopausal symptoms.

Although menopausal symptoms vary from person to person, it has been reported that a great number of women experience menopausal symptoms, and the severer the degree thereof and longer the period thereof, the lower the quality of their lives. In addition, menopausal symptoms are likely to proceed into chronic diseases together with aging of the body.

Treatment of menopausal symptoms may include hormone therapy, pharmacotherapy, exercise therapy, dietary therapy, and the like. Among these, medically and substantially used female hormone therapy may increase the risk of breast cancer and the like, and may increase the rate of uterine cancer, thrombotic diseases, gallbladder diseases, and hypertension during long-term use. Thus, research on phytoestrogen, which is reported to have estrogen-like functions to replace estrogen therapy, other drug therapies, and the like, has recently been actively conducted.

Previous studies related to improvement of menopausal symptoms disclose a functional food for the alleviation of menopausal symptoms which includes, as main ingredients, Angelica gigas NAKAI, Ligusticum chuanxiong HORT., Paeonia japonica (Makino) Miyabe et Takeda, white atractylis, white Poria cocos, red ginseng, and a soybean extract, and a food including, as main ingredients, milk vetch roots, cassia seeds, kudzu, and a soybean extract and having an effect of alleviating female menopausal symptoms.

Therefore, the inventors of the present invention continuously studied and developed natural substances capable of effectively alleviating overall menopausal symptoms and osteoporosis due to the menopause, thus completing the present invention.

SUMMARY OF THE INVENTION

An object of the present invention is to provide a composition for effectively preventing, alleviating, or treating female overall menopausal symptoms and/or osteoporosis.

The prevent invention provides a composition for the prevention, treatment, or alleviation of menopausal symptoms and/or osteoporosis which includes: a Puerariae Flos extract; and an extract of one or more selected from the group consisting of Citri Fructus Aurantii and Citri Pericarpium.

The composition may be a food composition, a pharmaceutical composition, or a composition for skin external application.

The present invention also provides a health functional food including the above-described extract.

The present invention also provides a cosmetic, a drug, and/or a skin external application including the above-described composition.

According to the present invention, a composition is rapidly effective in preventing or alleviating female menopausal symptoms and/or osteoporosis, and thus may be usefully used in conventional hormone replacement therapy (HRT) used to prevent or alleviate menopausal symptoms. In addition, the composition according to the present invention has no toxicity, can be used as food due to few side effects, and is safe, unlike conventional therapeutic agents for female menopausal symptoms or osteoporosis, and thus can be widely used as a therapeutic agent for female menopausal symptoms and/or osteoporosis.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The present invention relates to a composition for the prevention, alleviation, or treatment of menopausal symptoms which includes: a Puerariae Flos extract; and an extract of one or more selected from the group consisting of Citri Fructus Aurantii and Citri Pericarpium.

The present invention also provides a composition for the prevention, alleviation, or treatment of osteoporosis which includes: a Puerariae Flos extract; and an extract of one or more selected from the group consisting of Citri Fructus Aurantii and Citri Pericarpium.

Hereinafter, the composition according to the present invention will be described in more detail.

In one embodiment of the present invention, it was experimentally confirmed that, when a breast cancer cell line (MCF-7 cell line) was treated with a mixture of a Puerariae Flos extract and a Citri Fructus Aurantii or Citri Pericarpium extract, cell viability was enhanced, and, as a result of direct administration of the extract of the present invention, by utilization of the Kupperman index, menopausal symptoms were alleviated (see Experimental Examples 1 and 5). In addition, it was experimentally confirmed that, when osteoblast-like cells (MG-63 cells) were treated with the extract mixture of the present invention, the proliferation of osteoblasts was promoted, while the proliferation of osteoclasts was inhibited (see Experimental Examples 2 to 4).

Since the extract mixture of the present invention may treat or alleviate both menopausal symptoms and osteoporosis, the composition of the present invention may be a composition for preventing, treating, or alleviating menopausal symptoms and/or osteoporosis which includes: a Puerariae Flos extract; and an extract of one or more selected from the group consisting of Citri Fructus Aurantii and Citri Pericarpium.

As described above, the composition for preventing or alleviating menopausal symptoms and/or osteoporosis includes the extract mixture. The extract mixture includes: a Puerariae Flos extract; and an extract of one or more selected from the group consisting of Citri Fructus Aurantii and Citri Pericarpium. More particularly, the extract mixture may be a mixture of the Puerariae Flos extract and the Citri Fructus Aurantii extract, a mixture of the Puerariae Flos extract and the Citri Pericarpium extract, or a mixture of the Puerariae Flos extract, the Citri Fructus Aurantii extract, and the Citri Pericarpium extract.

The extract mixture may include 1 part by weight to 100 parts by weight of an extract of one or more selected from the group consisting of Citri Fructus Aurantii and Citri Pericarpium with respect to 10 parts by weight of the Puerariae Flos extract (a weight ratio of the Puerariae Flos extract and an extract of one or more selected from the group consisting of Citri Fructus Aurantii and Citri Pericarpium 10:1 to 100). Preferably, the extract mixture may include 5 parts by weight to 50 parts by weight, more preferably, 8 parts by weight to 20 parts by weight, of an extract of one or more selected from the group consisting of Citri Fructus Aurantii and Citri Pericarpium with respect to 10 parts by weight of the Puerariae Flos extract. In one embodiment of the present invention, it is confirmed that, when the mixture of the Puerariae Flos extract and the Citri Fructus Aurantii extract or the mixture of the Puerariae Flos extract and the Citri Pericarpium extract is used, the extract mixture exhibited a more excellent effect of alleviating or preventing menopausal symptoms and osteoporosis, as compared to a single extract.

The term 'Puerariae Flos' as used herein refers to the flower of Pueraria lobate, which is herbaceous perennial vine belonging to the family Leguminosae and a traditional herbal medicine widely used in herbal clinic. This term is also referred to as Pueraria lobate. Ingredients of Puerariae Flos include various compounds belonging to the isoflavone family. Puerariae Flos may be buds that do not bloom.

The term 'Citri Fructus Aurantii' as used herein refers to fruits of Citrus aurantium, Citrus natsudaidai, or a cultivated variant thereof that belongs to the family Rutaceae. Preferably, Citri Fructus Aurantii may be an immature fruit. It has been reported that a variety of compounds as main ingredients belonging to the flavanone and flavonoid families were isolated and are effective in antioxidation and anti-inflammation. Non-limiting examples of Citri Fructus Aurantii include Aurantium acre, Aurantium bigarella, Aurantium corniculatum, Aurantium coronatum, Aurantium distortum, Aurantium humile, Aurantium myrtifolium, Aurantium orientale, Aurantium Silvestre, Aurantium sinense, Aurantium variegatum, Aurantium vulgare, Citrus bigaradia, Citrus humilis, Citrus amara, Citrus aurata, Citrus benikoji, Citrus calot, Citrus canaliculata, Citrus changshan-huyou, Citrus communis, Citrus dulcimedulla, Citrus dulcis, Citrus florida, Citrus funadoko, Citrus fusca, Citrus glaberrima, Citrus humilis, Citrus intermedia, Citrus iwaikan, Citrus iyo, Citrus karna, Citrus keraji, Citrus kotokan, Citrus medioglobosa, Citrus mitsuharu, Citrus myrtifolia, Citrus natsudaidai, Citrus omikanto, Citrus pseudogulgul, Citrus reshni, Citrus rokugatsu, Citrus rumphii, Citrus sinograndis, Citrus subcompressa, Citrus sulcata, Citrus taiwanica, Citrus tangelo, Citrus tengu, Citrus tosa-asahi, Citrus truncate, Citrus vulgaris, Citrus yatsushiro, and Citrus yuge-hyokan.

The term 'Citri Pericarpium' as used herein refers to the pericarp of Citrus unshiu Markovich or fruits of closely related congeneric plants. Also, Citri Pericarpium may be the pericarp of Citrus reticulata Blanco and fruits of cultivated variants thereof. It tastes bitter and spicy and has warm properties, and is used for vomiting, nausea, indigestion, and the like that occur due to a weak stomach.

Puerariae Flos, Citri Fructus Aurantii, or Citri Pericarpium of the present invention may be commercially available, or cultivated or collected from the wild. In addition, Puerariae Flos, Citri Fructus Aurantii, or Citri Pericarpium includes dried and crushed forms regardless of the shape thereof.

The extract of the present invention may be extracted from a subject to be extracted such as a plant body, or the like after being treated with an extraction solvent, or may be prepared by applying a fractionation solvent to an extract obtained by extraction with an extraction solvent to be fractionated.

The extract or fraction includes an extract itself, such as a diluted or concentrated form of the extract, a dried product obtained by drying the extract, a crude-purified or purified product of the extract, mixtures thereof, and the like, and all preparations that can be formulated using such extracts. In particular, the extract of the present invention may be prepared in a dried form after being extracted. In addition, after the extraction or fractionation process, vacuum filtration may be performed or concentration and/or lyophilization may be further performed to concentrate the extract or fraction or remove the solvent therefrom. The obtained extract may be stored in a deep freezer until used.

The subject to be extracted, used in the extract of the present invention, includes embryoid bodies and cultures of tissues using natural, crossbred or variant plants and cells.

The type of the extraction solvent is not particularly limited, and any solvent known in the art may be used as long as it allows an extract with desired effects of the present invention to be obtained. In particular, the extraction solvent may be one or more selected from the group consisting of water and an organic solvent. The organic solvent may be one or more solvent selected from the group consisting of C1-C5 alcohols such as methanol, ethanol, and the like, ethyl acetate, acetone, and chloroform.

The extraction solvent is preferably water. In a particular embodiment, a degree to which menopausal symptoms are alleviated using a mixture of a Puerariae Flos extract and a Citri Fructus Aurantii or Citri Pericarpium extract, obtained using purified water, is evaluated, from which it is confirmed that viability, osteoblast differentiation, and proliferation ability of cells treated with the extract mixture are enhanced, and experimental groups administered the extract mixture exhibit alleviated menopausal symptoms.

The fractionation solvent may be water, butanol, ethyl acetate, ether, chloroform, benzene, hexane, methylenechloride, or a mixture thereof. The fraction may be an extract prepared using the above-described extraction method, in particular, a fraction prepared by further fractionating a crude extract. The fractionation process may be performed by, for example, sequentially applying hexane, chloroform, ethyl acetate, butanol, and water to a crude extract, and then sequentially obtaining a hexane fraction, a chloroform fraction, an ethyl acetate fraction, a butanol fraction, and a water fraction that are separated into layers.

The method of preparing the extract of the present invention is not particularly limited, and the extract may be obtained using any method commonly used in the art. Non-limiting examples of the extraction method include hot water extraction, ultrasonic extraction, filtration, and reflux extraction, and these methods may be performed alone or two or more of these methods may be performed in combination. In addition, the extract may be subjected to extraction once or more in the same manner to obtain a high-purity extract.

The term 'menopausal symptoms' collectively refers to symptoms and illnesses of women before or after menopause as estrogen secretion decreases due to aging of ovaries, or the like. This term is also referred to as climacteric syndrome or menopausal symptoms. For example, the climacteric or menopausal symptoms include facial blushing, perspiration, nervousness, depression, giddiness, fatigue, arthralgia, muscular aches, headaches, heart palpitations, formication, sweating during sleep, sleeping disorders, dry skin, vaginal dryness, vaginal atrophy, atrophy of the lower urethra, dyspareunia, vaginitis, cystitis, dysuria, cramps, concentration disorders, memory disorders, anxiety, hypersensitivity, memory loss, skin dryness, arthralgia, and osteoporosis, but the present invention is not limited thereto. In addition, cardiovascular disorders such as heart disease, hypertension, and stroke may also be one of the menopausal symptoms.

The term 'osteoporosis' as used herein refers to a condition in which fractures are highly likely to occur because the bones become weak, and is caused by genetic factors, early menopause, drugs, smoking, or the like. Thus, this term may refer to menopausal osteoporosis occurring due to a decrease in hormone production by menopause of women, or the like. Menopausal osteoporosis refers to symptoms of osteoporosis occurring in postmenopausal women due to an imbalance between osteoblasts involved in bone formation and osteoclasts involved in destruction and absorption of tissue, caused by a decrease in hormone production.

The term 'prevention' as used herein means all actions that inhibit or delay targeted symptoms via administration of the composition of the present invention.

The term 'treatment' as used herein means all actions that alleviate or relieve targeted symptoms or diseases via administration of the composition of the present invention.

The term 'alleviation' as used herein means all actions that alleviate or beneficially change targeted symptoms via administration of the composition of the present invention, as compared to the administration.

The extract may be included in the composition of the present invention in an effective amount. The term 'effective amount' as used herein refers to an amount of the extract sufficient to inhibit or delay menopausal symptoms or osteoporosis, to alleviate the ongoing symptoms, or to exhibit an effect of promoting the differentiation and proliferation of osteoblasts.

The extract mixture may be included in the composition in a variety of amounts, as an effective amount that enables the prevention, alleviation, or treatment of menopausal symptoms or osteoporosis. In particular, the amounts of the Puerariae Flos extract, the Citri Fructus Aurantii extract, and the Citri Pericarpium extract may be 0.001 wt % to 30 wt %, 0.001 wt % to 30 wt %, and 0.001 wt % to 30 wt %, respectively, based on a total weight of the composition. In addition, the amount of the extract mixture included in the composition of the present invention may be 0.01 wt % or more, for example, 0.1 wt % or more, preferably, 10 wt % or more, with respect to the total weight of the composition. When the amount of the extract mixture is within the above-described ranges, a more excellent effect of preventing or alleviating menopausal symptoms or osteoporosis may be obtained.

When each effective ingredient is included in an amount of less than the lower limit, the efficacy of preventing, treating, or alleviating menopausal symptoms or osteoporosis may not be exhibited. On the other hand, when each effective ingredient is included in an amount of greater than the upper limit, physical properties, color, and unique flavors of the effective ingredients themselves may adversely affect products.

In addition, in one embodiment of the present invention, the composition may include 1 mg to 1000 mg, preferably, 5 mg to 500 g, more preferably, 10 mg to 300 g, of the extract of the present invention with respect to 1 kg of the composition.

The composition according to the present invention may be a food composition for preventing or alleviating menopausal symptoms or osteoporosis.

The present invention also provides a food for preventing or alleviating menopausal symptoms or osteoporosis which includes the above-described composition.

Puerariae Flos, Citri Fructus Aurantii, and Citri Pericarpium included in the food composition of the present invention are natural substances and have long been used and thus stability thereof has been verified. In addition, these substances can be generally prepared in the form of an ingestible food to be ingested, and thus may be expected to be highly effective in preventing or alleviating menopausal symptoms or osteoporosis.

In one particular embodiment, it was experimentally confirmed that a group of subjects who was administered soft capsules including both the Puerariae Flos extract and the Citri Fructus Aurantii or Citri Pericarpium extract exhibited alleviated menopausal symptoms.

The term 'food' as used herein refers to a natural substance or processed product including one or more nutrients. Preferably, the food refers to a food in a state of being directly eaten through a certain degree of processing. In addition, the food generally includes health functional foods, functional foods, beverages, food additives, and beverage additives.

The food includes all general foods. For example, the foods may be various kinds of foods, beverages, gum, tea, vitamin complexes, health functional foods, or the like. In addition, the food of the present invention includes special nutrition foods (e.g., milk formulas, infant meals, and the like), processed meat products, fish meat products, bean curds, jellied foods, noodles (e.g., instant noodles, pastas, and the like), health supplement foods, seasonings for food (e.g., soy sauce, soybean paste, red pepper paste, mixed soy paste, and the like), sauces, confectionaries (e.g., snacks), dairy products (e.g., fermented milk, cheese, and the like), other processed foods, kimchi, pickled foods (e.g., fermented vegetables, pickled vegetables, and the like), beverages (e.g., fruit and vegetable beverages, soybean milk products, fermented drinks, and the like), flavor enhancers (e.g., ramen soup bases, and the like), but the present invention is not limited thereto.

The foods, the functional foods, the health functional foods, the beverages, the food additives, and the beverage additives may be prepared using general preparation methods.

In the present invention, the health functional food refers to a group of foods having added values provided by a physical, biochemical, or biotechnological method so that the corresponding food imparts or exhibits intended functions suitable for specific applications, or a processed food designed such that a composition of the food sufficiently imparts, in the body, body modulation functions regarding biological defense rhythm control, disease prevention and restoration, and the like. The health functional food has a more aggressive effect of maintaining or promoting health, and the health supplement food refers to a food for the purposes of health supplementation. In some cases, the terms "functional food", "health food", and "health supplement food" are interchangeably used. The term "functional food" as used herein is interchangeably used with the term "food for special health use (FoSHU)", and refers to a food with excellent medical effects processed so as to effectively exhibit body modulation functions in addition to nutrient supply. The term "functional" as used herein means acquisition of effectiveness in health applications such as regulation of nutrients, physiological functions, or the like with respect to the structure and function of the human body. The functional food of the present invention may be prepared using methods commonly used in the art, and may be prepared by adding raw materials and ingredients commonly added in the art. The food composition of the present invention may be prepared in various types of formulations, and uses foods as raw materials unlike generic medicines, resulting in no side effects and the like that may occur due to long-term use of drugs, and is highly portable, and, accordingly, the food composition is easily administered as an adjuvant for promoting an effect of preventing or alleviating menopausal symptoms or osteoporosis.

In particular, the health functional food refers to a food prepared by adding the extract of the present invention or a fraction thereof to a food substance, such as beverages, teas, flavor enhancers, gums, confectionaries, and the like, or a food prepared into capsules, powder, suspensions, or the like using the extract of the present invention or a fraction thereof, and means that, when the food is administered, specific effects in terms of health are obtained. However, unlike generic drugs, the health functional food uses foods as raw materials, and thus has no side effects that may occur due to long-term use of drugs.

The amount of the composition in the health functional food of the present invention may be 0.001 wt % to 70 wt %, preferably, 0.01 wt % to 50 wt % or 0.1 wt % to 30 wt %, with respect to a total weight of the health functional food.

The food may include a sitologically acceptable food supplement additive, and may further include suitable carriers, excipients, and diluents commonly used to prepare a health functional food.

The composition may include an additional ingredient commonly used in food compositions to enhance smell, taste, appearance, and the like. For example, the additional ingredient may include vitamins A, C, D, E, B 1, B2, B6, and B12, niacin, biotin, folate, panthotenic acid, and the like. In addition, the additional ingredient may include minerals such as zinc (Zn), iron (Fe), calcium (Ca), chromium (Cr), magnesium (Mg), manganese (Mn), copper (Cu), and the like. In addition, the additional ingredient may include amino acids such as lysine, tryptophan, cysteine, valine, and the like.

The composition may include food additives such as preservatives (e.g., potassium sorbate, sodium benzoate, salicylic acid, sodium dehydroacetate, and the like), disinfectants (e.g., bleaching powder and high-grade bleaching powder, sodium hypochlorite, and the like), antioxidants (butylhydroxyani sole (BHA), butylhydroxytoluene (BHT), and the like), colorants (tar pigments, and the like), color fixing agents (sodium nitrite, sodium acetate, and the like), a bleaching agent (sodium sulfite), seasonings (monosodium glutamate (MSG), and the like), sweeteners (dulcin, cyclamate, saccharin, sodium, and the like), flavorings (vanilla, lactones, and the like), swelling agents (alum, potassium hydrogen D-tartrate, and the like), a reinforcing agent, an emulsifying agent, a thickener (filler), a coating agent, a gum base agent, an antifoaming agent, a solvent, an improving agent, and the like. The additives may be selected according to the type of food and used in appropriate amounts.

In the case of a composition including the extract of the present invention or a fraction thereof, the composition may appropriately include the extract or the fraction thereof alone or in combination with other foods or food ingredients according to a commonly used method. A mixing amount of active ingredients may be appropriately determined according to the purposes of use (prevention, health or medical treatment). In general, in preparation of foods or beverages, the food composition of the present invention may be added in an amount of 30 parts by weight or less, preferably, 20 parts by weight or less, with respect to raw materials. However, when ingested for a long period of time for health and hygiene purposes, the food composition may be included in an amount in or less than the above ranges of amounts. The food composition has no problem in terms of safety, and thus may also be used in an amount in or greater than the above ranges of amounts.

The food composition of the present invention may be, for example, a health beverage composition.

The term "beverage" as used herein collectively refers to drinks for relieving thirst and enjoying a taste, and includes health functional beverages.

The beverage includes, as an essential ingredient, the extract of the present invention as an active ingredient, and other ingredients thereof are not particularly limited. In addition, the beverage may include, as additional ingredients, various flavoring agents, natural carbohydrates, or the like as in general beverages.

The natural carbohydrates may be, for example, monosaccharides such as glucose, fructose, and the like, disaccharides such as maltose, sucrose, and the like, polysaccharides such as dextrin, cyclodextrin, and the like, sugar alcohols such as xylitol, sorbitol, erythritol, and the like, or the like. The flavoring agents may be natural flavoring agents such as a stevia extract such as thaumatin, rebaudioside A, or glycyrrhizin, or synthetic flavoring agents such as saccharin, aspartame, and the like.

The natural carbohydrates may be added generally in an amount of about 1 g to about 20 g, preferably, 5 g to 12 g, based on 100 ml of the food composition of the present invention, but the present invention is not limited thereto. In addition, the composition of the present invention may further include flesh for the preparation of natural fruit juice, fruit juice beverages, and vegetable beverages.

In addition to the above-listed ingredients, the food composition of the present invention may include additives such as various nutritional supplements, vitamins, minerals (electrolytes), flavors such as synthetic flavors, natural flavors, and the like, colorants and enhancers (enhancers: cheese, chocolates, and the like), pectic acid and salts thereof, alginic acid and salts thereof, organic acids, a protective colloid thickener, a pH adjusting agent, a stabilizer, a preservative, glycerin, alcohols, a carbonating agent used in carbonated beverages, and the like. The proportion of these additives is not much important, but the amounts of the additives are generally selected from 0.01 parts by weight to 0.1 parts by weight based on 100 parts by weight of the composition of the present invention.

The health functional beverages refer to a group of beverages having added values provided by a physical, biochemical, or biotechnological method so that the corresponding beverages impart or exhibit intended functions suitable for specific applications, or processed beverages designed such that a composition of the beverages sufficiently imparts, in the body, body modulation functions regarding biological defense rhythm control, disease prevention and restoration, and the like.

The health functional beverage includes the extract of the present invention as an essential ingredient, and other ingredients thereof are not particularly limited. In addition, the health functional beverage may include, as additional ingredients, various flavoring agents, natural carbohydrates, or the like as in general beverages.

The food may further include food additives and, unless otherwise prescribed, the suitability of food additives is determined by the specification and standard of the concerned item in accordance with general provisions and general test methods of the Korean Food Additives Codex approved by the Korean Food and Drug Administration.

In addition, the composition according to the present invention may be a pharmaceutical composition for the prevention or treatment of menopausal symptoms or osteoporosis which includes the extract mixture.

The present invention also provides a drug or quasi-drug including the above-described pharmaceutical composition.

In one embodiment, it was confirmed that, when an MCF-7 cell line, which is a breast cancer cell line, was treated with the extract mixture of the present invention, cell viability was enhanced, and it was experimentally confirmed using the Kupperman index that, as a result of directly taking the extract of the present invention, menopausal symptoms were alleviated (see Experimental Examples 1 and 5). In addition, it was experimentally confirmed that, when MG-63 cells, which are osteoblast-like cells, were treated with the extract mixture of the present invention, the proliferation of osteoblasts was promoted, whereas, in the case of osteoclasts, the proliferation thereof was inhibited (see Experimental Examples 2 to 4).

The term "pharmaceutical composition" as used herein refers to a composition for the diagnosis, therapy, alleviation, medical treatment, or prevention of diseases of animals including humans.

The extract of the present invention may be included in the composition in an amount effective in preventing, alleviating, or treating menopausal symptoms or osteoporosis. In particular, the amounts of the Puerariae Flos extract, the Citri Fructus Aurantii extract, and the Citri Pericarpium extract in the composition may be 0.001 wt % to 30 wt %, 0.001 wt % to 30 wt %, and 0.001 wt % to 30 wt %, respectively, with respect to a total weight of the composition. When each ingredient is included in an amount less than the lower limit, an effect of preventing or treating menopausal symptoms may not be exhibited, and, when each ingredient is included in an amount greater than the upper limit, physical properties, color, and unique flavors of the ingredients themselves may adversely affect products.

In addition, the pharmaceutical composition of the present invention may be used alone or in combination with other pharmaceutical active ingredients that exhibit an effect of preventing or treating menopausal symptoms and/or osteoporosis.

The composition of the present invention may be administered to an individual in a pharmaceutically effective amount. The term "pharmaceutically effective amount" as used herein refers to an amount sufficient to treat diseases at a reasonable benefit/risk ratio applicable to medical treatment and not cause side effects, and an effective dosage level may be determined according to factors including health conditions of patients, type of diseases of patients, the severity of diseases, the activity of drugs, sensitivity to drugs, administration method, administration time, administration route, excretion rate, treatment period, drugs that are formulated or co-administered, and other factors well known in medical fields. In particular, the composition of the present invention may be administered to an individual generally in an amount of 0.01 mg to 5000 mg per body weight (1 kg) of the individual daily, and may be administered once or several times a day at regular time intervals according to the prescription of a doctor or a pharmacist, but the present invention is not limited thereto.

The composition may be administered to mammals including rats, mice, livestock, humans, and the like via various routes such as parenteral administration, oral administration, and the like. All administration methods can be expected, for example, oral injection, rectal or intravenous injection, muscular injection, subcutaneous injection, intrauterine epidural injection, and intracerebroventricular injection.

The pharmaceutical composition of the present invention may include the above-described extract alone as an active ingredient, and may further include a pharmaceutically acceptable carrier, an excipient, a diluent, and/or an accessory ingredient according to formulation, usage form, and usage purpose.

More particularly, the pharmaceutical composition may further include, in addition to the active ingredient, nutritional supplements, vitamins, electrolytes, flavoring agents, colorants, enhancers, pectic acid and salts thereof, alginic acid and salts thereof, organic acids, protective colloid thickeners, pH adjusting agents, stabilizers, preservatives, glycerin, alcohols, carbonating agents used in carbonated beverages, and the like.

The term "pharmaceutically acceptable" as used herein refers to physiologically acceptable and means that, when administered to an animal, preferably, a human, generally, gastrointestinal disorders, allergic reactions such as dizziness, or reactions similar thereto do not occur.

For example, the pharmaceutically acceptable carrier, the excipient, or the diluent may be one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, dextrin, calcium carbonate, propylene glycol, liquid paraffin, and physiological saline, but the present invention is not limited thereto. That is, commonly used carriers, excipients, or diluents may also be used.

One or a combination of the above-listed ingredients may be added to the extract, which is an active ingredient.

Preparations of the pharmaceutical composition may vary depending on the method of use and may be formulated using methods well known in the art to which the present invention pertains to provide rapid, sustained or delayed release of the active ingredient after being administered to a mammal. The preparations may be, for example, preparations selected from the group consisting of ointments, creams, tablets, pills, powders, granules, capsules, suspensions, liquids for internal use, emulsions, syrups, aqueous solutions, non-aqueous solvents, and oil solutions.

For the preparations, the pharmaceutical composition may further include excipients, for example, general fillers, extenders, binders, disintegrating agents, surfactants, anticoagulants, lubricants, wetting agents, flavoring agents, emulsifiers, preservatives, sweetening agents, fragrances, or the like.

Generally, solid preparations for oral administration include tablets, caplets, soft or hard capsules, pills, powders, granules, and the like. These preparations may be formulated in combination with one or more excipients, for example, starch, calcium carbonate, sucrose, lactose, gelatin, and the like. In addition to simple excipients, lubricants such as magnesium stearate or talc may also be used.

In addition, liquid preparations for oral administration include suspensions, liquids and solutions for internal use, emulsions, syrups, and the like, and may include various excipients, for example, wetting agents, sweetening agents, fragrances, preservatives, and the like, in addition to commonly used simple diluents such as water or liquid paraffin.

Examples which may be mentioned for dermal administration include carriers and/or excipients suitable for preparing dusting powders, emulsions, suspensions, oils, sprays, ointments, greasy ointments, cream pastes, gels, foams, or solutions, and suitable for transdermal therapeutic systems (TTSs). Topical pharmaceutical preparations of the present invention may be semi-solid formulations, in particular, ointments (solution ointment and suspension ointment), creams, gels, or pastes. Examples mainly used for oil phases include fatty alcohols such as lauryl alcohol, cetyl alcohol, and stearyl alcohol, fatty acids such as palmitic acid and stearic acid, liquid or solid paraffin or ozokerite, liquid- or solid-phase waxes such as isopropyl myristate, natural fats or partially synthetic fats such as coconut fatty acid triglycerides, hydrogenated oils such as hydrogenated peanut and castor oil, and fatty acid partial esters of glycerol such as glycerol monostearate and glycerol distearate. Suitable emulsifiers include surfactants, for example, non-ionic surfactants such as polyalcohols or fatty acid esters of ethylene oxide adducts thereof, e.g., polyglycerol fatty acid esters or polyoxyethylene sorbitan fatty acid esters, sorbitan fatty acid esters, e.g., sorbitan oleate and/or sorbitan isostearate, isostearate, sterols, or polyoxyethylene fatty alcohol ethers or fatty acid esters; and anionic surfactants such as alkaline metal salts of fatty alcohol sulfonates, e.g., sodium lauryl sulfate, sodium cetyl sulfate, or sodium stearyl sulfate. These surfactants are generally used in the presence of the above fatty alcohol, for example, cetyl alcohol or stearyl alcohol. Among these, in particular, preparations for preventing drying of creams, for example, polyalcohols such as glycerol, sorbitol, propylene glycol, and/or polyethylene glycol may be added to a water phase or preservatives, flavorings, or the like may be added to a water phase.

The pharmaceutical preparations of the present invention may be anhydrous ointments, and may include paraffin, which is suitable for topical application and is liquid at body temperature, in particular, low-viscosity paraffin, or the natural fats or partially synthetic fats, e.g., coconut fatty acid triglycerides, hydrogenated oils such as hydrogenated peanut or castor oil, fatty acid partial esters of glycerol, e.g., glycerol monostearate and distearate, silicones such as polymethylsiloxanes, e.g., hexamethylsiloxane or octamethyltrisiloxane. For example, the pharmaceutical preparations may include fatty alcohols that are associated with water-based cream and increase water absorption capacity, sterols, wool waxes, other emulsifiers and/or other additives.

In the present invention, when the pharmaceutical composition is formulated as a drug, contents disclosed in Remington's Pharmaceutical Science, Mack Publishing Company, Easton Pa. may be referred to, and the documents are incorporated herein in its entirety by reference.

The pharmaceutical composition may be a quasi-drug composition.

The term "quasi-drug" as used herein means any one of the following commodities: fibers, rubber products or similar products used for the purpose of treatment, alleviation, medical care, or prevention human or animal diseases; non-appliance, non-machinery or similar commodities that have insignificant influences on or do not directly act upon human bodies; preparations used for sterilization, insecticide, and uses similar thereto for the purpose of preventing infectious diseases, and means products used for the purposes of diagnosis, medical care, alleviation, treatment, or prevention of diseases of human beings or animals, excluding appliances, machinery and equipment; and products, other than appliances, machinery or equipment, used for the purpose of exerting pharmacological effects upon the structure or functions of human beings or animals, in particular, preparations for external application to the skin or personal hygiene products, but the present invention is not limited thereto.

When the extract mixture or the fraction of the present invention is added to a quasi-drug composition to prevent or treat menopausal symptoms or osteoporosis, the extract or fraction may be added alone or in combination with other quasi-drug ingredients, and may be appropriately used according to a general method. A mixing amount of active ingredients may be appropriately determined according to the purpose of use.

The preparations for external application to the skin are not particularly limited, and may be prepared in the form of, for example, ointments, lotions, sprays, patches, creams, powders, suspensions, or gels. The personal hygiene products are not particularly limited, but may be, in particular, soap, cosmetics, wet tissue, tissue paper, shampoo, skin cream, face cream, toothpaste, lipstick, perfume, makeup, foundation, blusher, mascara, eye shadow, sunscreen lotion, hair care products, air freshener gel, or cleansing gel. In addition, other examples of the quasi-drug composition of the present invention include disinfectant cleaners, shower foams, wet tissue, detergent soap, hand wash, masks, or ointments.

In addition, the pharmaceutical composition of the present invention may be used alone for alleviation, relief, treatment, or prevention, or in combination with surgery, hormone treatment, drug treatment, and methods using biological response modifiers.

The present invention also provides a method of preventing or treating menopausal symptoms or osteoporosis, including administering, to an individual, a pharmaceutically effective amount of the composition for the prevention or treatment of menopausal symptoms or osteoporosis.

The terms "menopausal symptoms", "menopausal osteoporosis", "prevention", "treatment", and "administration" have been already described above.

Dosage, the frequency of administration, and administration routes for the above administration are the same as described above.

The term "individual" as used herein refers to all animals including humans, monkeys, cows, horses, sheep, pigs, chickens, turkeys, quails, cats, dogs, mice, rats, rabbits, or guinea pigs that have the menopausal symptoms or osteoporosis, or have a risk thereof, and the composition of the present invention may be administered to an individual, thereby effectively preventing or treating the disease.

In addition, the composition according to the present invention may be a composition for external application to the skin.

The composition for external application to the skin may be used for the prevention or alleviation of menopausal symptoms or osteoporosis. In particular, this composition may be used for the alleviation or prevention of symptoms such as skin dryness or facial blushing that appear due to menopause.

The description of the terms "menopausal symptoms", "menopausal osteoporosis", "alleviation", and "prevention" has already been provided above.

The composition for external application to the skin means as including all compositions for the preparation of drugs, quasi-drugs, or cosmetics. For example, the composition may be a cosmetic composition.

An effective amount of the extract included in the composition of the present invention may vary according to the type of products of the composition, methods by which the extract is applied to the skin, retention time of the composition on the skin, and the like.

For example, when the composition is manufactured as a drug for dermatological treatment, the drug composition may include the extract in a higher concentration than that when manufactured as a cosmetic applied to the skin daily. Even when the composition is manufactured as a cosmetic, in the case of wash-off type cosmetics in which active ingredients thereof remain on the skin for a short period of time, such as makeup removing agents, cleansing agents, and the like, the extract may be included in a relatively high concentration. In contrast, in the case of leave-on type cosmetics in which active ingredients thereof remain on the skin for a long period of time, such as tonics, milky lotions, creams, essences, and the like, the extract may be included in a lower concentration than that of such wash-off type cosmetics.

The composition may be formulated in any preparations that may be applied to the integument. For example, the preparations may be selected from the group consisting of ointments, plasters, patches, liquids and solutions, suspensions, emulsions, pastes, gels, creams, lotions, powders, soaps, surfactant-containing cleansings, oils, foundations, tonics, cosmetic ointment, sprays, packs, sunscreens, makeup bases, makeup powders, makeup removers, and cleansing agents, but the present invention is not limited to the above examples.

The composition for external application, including the extract according to the present invention, may further include a cosmetically acceptable carrier, a diluent, an adjuvant, a colorant, a stabilizer, a flavoring agent, a surfactant, oils, a moisturizing agent, alcohols, a thickener, an antioxidant, a pH adjuster, a sunscreen, and the like to facilitate use and handling. When the composition including the extract according to the present invention is used as a composition for external application to the skin, the composition may be formulated in any preparations that may be applied to the integument, such as liquids and solutions, oils, creams, ointments, stick forms, packs, pastes, powders, and the like. In addition, the compositions may include one or two or more of the above-listed materials.

When the composition for external application is formulated as a cosmetic, the composition may include a known dermatologically acceptable excipient that acts as a carrier for active ingredients. In particular, contents disclosed in International Cosmetic Ingredient Dictionary, 6th ed., the Cosmetic, Toiletry and Fragrance Association, Inc., Washington, 1995 may be referred to, and the documents are incorporated herein in its entirety by reference.

The present invention also provides a cosmetic including the extract mixture as an active ingredient.

The cosmetic may have any one preparation selected from the group consisting of tonics, essences, skins, lotions, creams, and packs.

The cosmetic may be, for example, toner, skin softener, skin toner, astringent, lotion, milk lotion, moisturizing lotion, nutrition lotion, massage cream, nourishing cream, moisturizing cream, hand cream, foundation, essence, nutrition essence, pack, cleansing foam, cleansing lotion, cleansing cream, body lotion, body cleanser, and the like, but the present invention is not limited to the above examples.

The numerical values described in the present specification should be construed as including equivalent ranges unless otherwise specified.

Hereinafter, the present invention will be described in further detail with reference to examples to aid in understanding of the present invention. However, the examples of the present invention may be modified in many different forms, and should not be construed as limiting the scope of the present invention. The examples of the present invention are provided so that the invention will be more fully explained to those of ordinary skill in the art.

EXAMPLES

Preparation Example 1

Preparation of Extract for In Vitro Experiments

Ethanol extracts were used in the following examples and purchased from OBM Lab. Extracts were prepared through a raw material introduction process to mix raw materials with 100% of ethyl alcohol, a room-temperature extraction process, a filtering process to remove impurities, and a concentration process to reach 85% solid, and were used in in vitro cell experiments.

Preparation Example 2

Preparation of Soft Capsules for Clinical Evaluation using Kupperman Index Experiments Soft capsules for clinical evaluation were prepared through, largely, a process of preparing main ingredients (menopausal substances) and a process of preparing soft capsules.

First, a main ingredient was prepared by applying a 10-fold amount of purified water to a dried powder sample of Puerariae Flos and performing extraction thereon at 80° C. for 6 hours using an extraction device. The extract was filtered using filter paper with a diameter of 160 mm, and the filtered extract was vacuum concentrated, followed by lyophilization, thereby completing preparation of the powder-type extract. A Citri Fructus Aurantii extract and a Citri Pericarpium extract were prepared in the same manner as described above.

Subsequently, the menopausal substances as main ingredients and excipients, i.e., soybean oil, beeswax, soybean lecithin, and D-α-tocopherol, were mixed and stirred, followed by removal of air bubbles, to prepare contents of soft capsules, and capsule bases were prepared by stirring purified water, a pigment, glycerin, modified starch, and carrageenan, and then the capsule bases were filled with the contents according to weight, followed by molding and drying, thereby completing preparation of soft capsules. Ratios of amounts of the contents of the soft capsules are shown in Table 1 below.

TABLE 1

| Raw material name | Comparative Example 1 | Comparative Example 2 | Comparative Example 3 | Comparative Example 4 | Example 1 | Example 2 |
|---|---|---|---|---|---|---|
| Puerariae Flos extract | — | 20 | — | — | 10 | 10 |
| Citri Fructus Aurantii extract | — | — | 20 | — | 10 | — |
| Citri Pericarpium extract | — | — | — | 20 | — | 10 |
| Soybean oil | 92.95 | 72.95 | 72.95 | 72.95 | 72.95 | 72.95 |
| Beeswax | 5 | 5 | 5 | 5 | 5 | 5 |
| soybean lecithin | 2 | 2 | 2 | 2 | 2 | 2 |
| D-α-tocopherol | 0.05 | 0.05 | 0.05 | 0.05 | 0.05 | 0.05 |

Experimental Example 1

Measurement of Cell Viability for MCF-7 Cells

Cell viability of the Citri Fructus Aurantii extract for an MCF-7 cell line, which is an estrogen receptor positive human breast cancer cell line, was measured. The CCK-8 assay using MCF-7 cells is an experimental method whereby the efficacy of naturally occurring female hormones in women can be confirmed. MCF-7 cells were cultured in a 96-well plate using DMEM media supplemented with 10% FBS. 24 hours after being cultured, the cultured cells were divided into groups including: a negative control (non-treated group), a positive control (estradiol-treated group, E2), and groups treated with one or a combination of the Puerariae Flos extract, the Citri Fructus Aurantii extract, and the Citri Pericarpium extract. After 72 hours, cell viability was measured using CCK-8. 10 μl of the CCK-8 reagent was treated per 100 μl of the medium and, after 1 hour, absorbance was measured at 450 nm. The results thereof are shown in FIG. 1.

Figure 1:
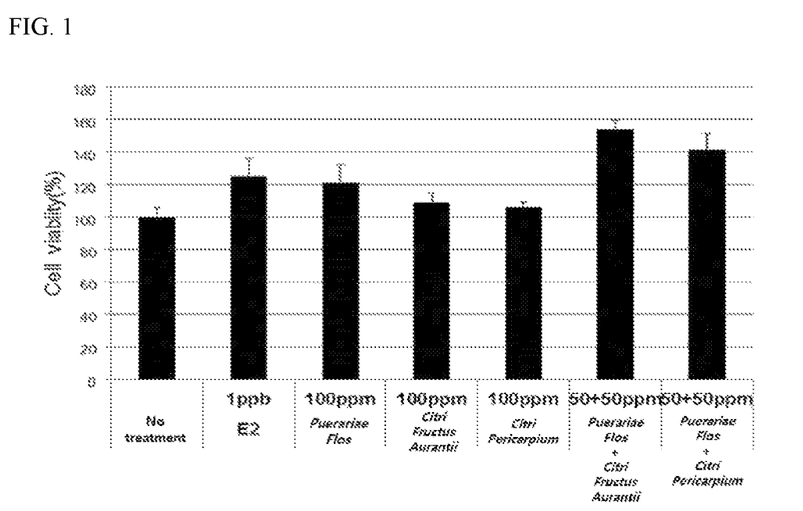
FIG. 1 is a graph showing cell viability of an extract according to an embodiment of the present invention with respect to an estrogen receptor-positive human breast cancer cell line.

As illustrated in FIG. 1, it was confirmed that all the extract-treated groups exhibited higher cell viability than that of the non-treated group (negative control), and, when treated with the combination of the Puerariae Flos extract and the Citri Fructus Aurantii extract or the Puerariae Flos extract and the Citri Pericarpium extract, cell viability was significantly higher than that in the groups treated with one of the three extracts.

Experimental Example 2

Effect of Promoting Proliferation of Osteoblast

To confirm an effect of promoting the proliferation of osteoblasts, the CCK-8 assay was performed on human osteoblast-like MG-63 cells.

An experiment was performed using, as experimental groups, a negative control (non-treated group), a positive control (estradiol-treated group, E2), groups treated with one of the extracts (Puerariae Flos extract, Citri Fructus Aurantii extract, and Citri Pericarpium extract), and groups treated with extract mixtures (Puerariae Flos+Citri Fructus Aurantii extract and Puerariae Flos+Citri Pericarpium extract).

First, a uniform number of MG-63 cells were cultured in a 96-well plate using an EMEM medium supplemented with 10% FBS. After 24 hours, the medium was replaced by a FBS-free EMEM medium, and a negative control (non-treated group) and a positive control (estradiol-treated group, E2) were used, the Puerariae Flos extract, the Citri Fructus Aurantii extract, and the Citri Pericarpium extract were treated alone, and the Puerariae Flos extract and the Citri Fructus Aurantii extract or the Puerariae Flos extract and the Citri Pericarpium extract were treated in a mixing ratio of 1:1. 48 hours after treatment, cell viability was measured using CCK-8. 10 μl of the CCK-8 reagent was treated per 100 μl of the medium and, after 1 hour, absorbance was measured at 450 nm. The results thereof are shown in FIG. 2.

Figure 2:
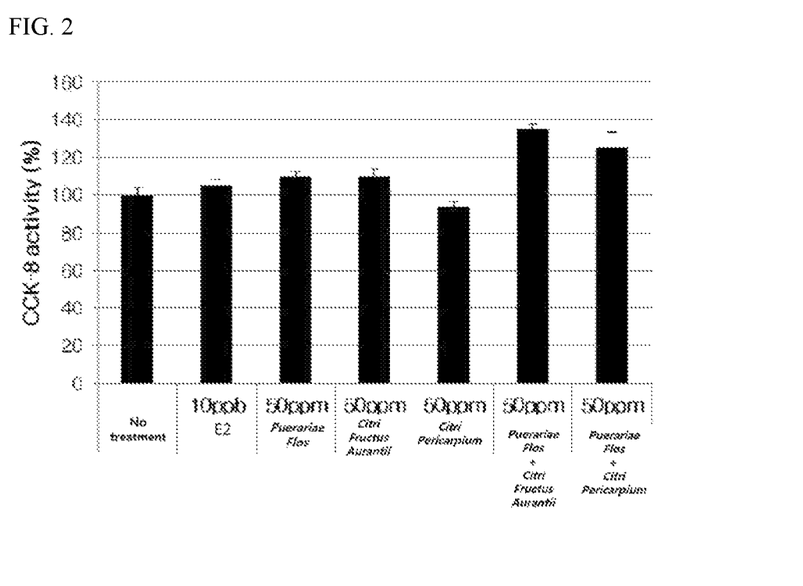
FIG. 2 is a graph showing an effect of promoting proliferation on osteobalsts by a mixed extract according to an embodiment of the present invention.

As illustrated in FIG. 2, it was confirmed that, when the extract mixture was treated, an effect of promoting the proliferation of osteoblasts was higher than that when each extract was treated alone, and much higher in the extract mixture-treated groups as compared to the positive control (E2).

Experimental Example 3

Effect of Promoting Differentiation of Osteoblast

To confirm an effect of each extract in promoting the differentiation of osteoblasts, ALP activity was measured using human osteoblast-like MG-63 cells.

Experimental groups were made in the same manner as in Experimental Example 2.

First, a uniform number of MG-63 cells were cultured in a 24-well plate using a DMEM medium supplemented with 10% FBS. After 24 hours, the medium was replaced by 10% charcoal stripped FBS containing a phenol red free medium, and a negative control (non-treated group) and a positive control (estradiol-treated group, E2) were used, the Puerariae Flos extract, the Citri Fructus Aurantii extract, and the Citri Pericarpium extract were treated alone, and the Puerariae Flos extract and the Citri Fructus Aurantii extract or the Puerariae Flos extract and the Citri Pericarpium extract were treated in a mixing ratio of 1:1. 3 days after culturing, the experimental groups were treated again with the same medium and the same concentrations of the extracts, and then further cultured for three days. After a total of 6 days of culturing, an assay was performed using a SensoLyte® pNPP Alkaline Phosphatase Assay Kit (ANASPEC AS-72146) to measure ALP activity. The cells were washed twice with an assay buffer, and 200 µl of a Triton X-100-containing assay buffer was added thereto, and then plates were placed on ice to be shaking-incubated for 10 minutes. A cell suspension was transferred to microcentrifuge tubes, and then centrifuged at 2500 ×g and 4° C. for 10 minutes, 50 µl of the supernatant and 50 µl of a pNPP substrate were added to a 96-well plate and a reaction was allowed to occur for 30 minutes, and absorbance was measured at 405 nm. The results thereof are shown in FIG. 3.

Figure 3:
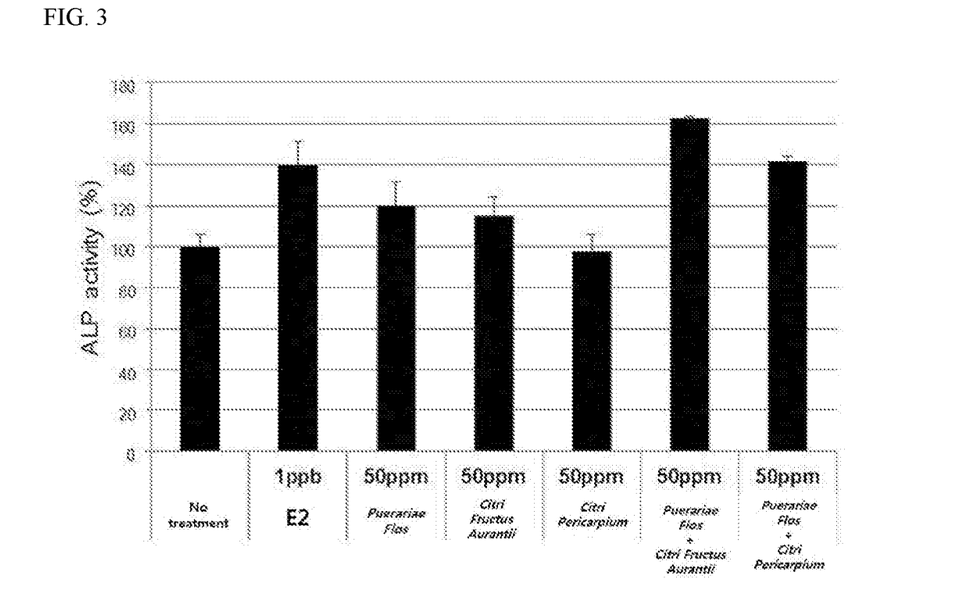
FIG. 3 is a graph showing an effect of promoting differentiation on osteoblasts by a mixed extract according to an embodiment of the present invention.

As illustrated in FIG. 3, it was confirmed that the differentiation of osteoblasts was more significantly promoted in the cell groups treated with the extract mixtures as compared to the case of the groups treated with each extract alone.

Experimental Example 4

Effect of Inhibiting Proliferation of Osteoclast

To confirm an effect of each extract in inhibiting the proliferation of osteoclasts, osteoclasts were cultured using a B-bridge® Rat Primary Precursor Osteoclasts Culture Kit, and then the CCK-8 assay was performed thereon. First, a uniform number of cells were seeded in a 96-well plate using a culture medium enclosed in the kit. Immediately after seeding, the Puerariae Flos extract, the Citri Fructus Aurantii extract, and the Citri Pericarpium extract were treated alone, and a mixture of the Puerariae Flos extract and the Citri Fructus Aurantii extract or a mixture of the Puerariae Flos extract and the Citri Pericarpium extract was treated according to concentration (10 ppm, 50 ppm, and 100 ppm), and a negative control (non-treated group) and a positive control (estradiol-treated group, E2) were used. 72 hours after treatment, cell viability was measured using CCK-8. 10 µl of the CCK-8 reagent was treated per 100 µl of the medium and, after 1 hour, absorbance was measured at 450 nm. The results thereof are shown in FIG. 4.

Figure 4:
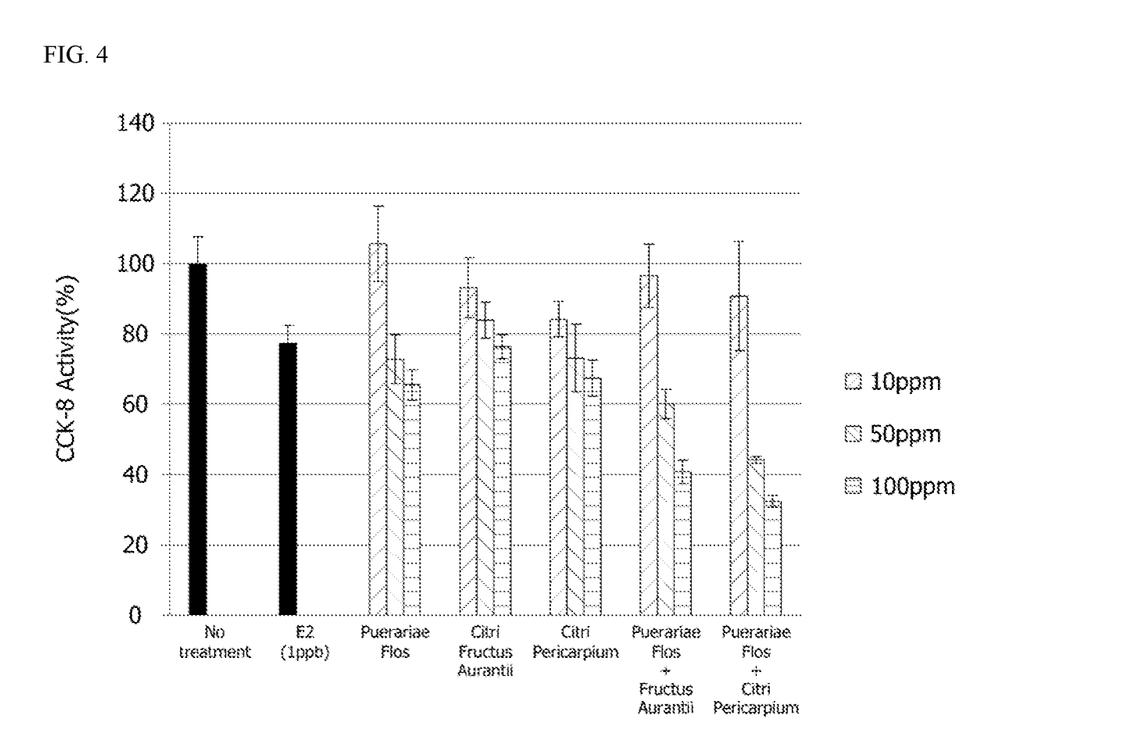
FIG. 4 is a graph showing an effect inhibiting proliferation of osteoclasts by a mixed extract according to an embodiment of the present invention.

As illustrated in FIG. 4, it was confirmed that the proliferation of osteoclasts was more effectively inhibited in the cell groups treated with the extract mixtures as compared to the groups treated with each extract. In particular, it was confirmed that an effect of the extract mixtures in inhibiting the proliferation of osteoclasts significantly increased in a concentration-dependent manner.

Experimental Example 5

Evaluation of Effect of Alleviating Menopausal Symptoms

Women with menopausal symptoms aged from late 40s to 50s were randomly divided and administered soft capsules prepared according to Comparative Examples 1 to 4 and Examples 1 and 2 in a daily dosage of 3 capsules for 8 weeks, and then an improvement degree of menopausal symptoms was evaluated.

Comparative Example 1 denotes a non-treated group, Comparative Example 2 denotes a Puerariae Flos extract-administered group, Comparative Example 3 denotes a Citri Fructus Aurantii extract-administered group, Comparative Example 4 denotes a Citri Pericarpium extract-administered group, Example 1 denotes a group administered a mixture of the Puerariae Flos extract and the Citri Fructus Aurantii extract, and Example 2 denotes a group administered a mixture of the Puerariae Flos extract and the Citri Pericarpium extract. In the case of the extract-treated groups, the amount of the extract (or the extract mixture) was 20 wt % with respect to a total weight of the composition.

A degree to which menopausal symptoms were alleviated 8 weeks after administration was measured using the Kupperman index, and, assuming that a value before administration was 100, relative values after administration are shown in Table 2 below.

The Kupperman index (KI) used in the present invention is a menopausal index used in academia and is obtained by scoring 11 symptoms (facial blushing, sweating, insomnia, nervousness, depression, dizziness, fatigue, joint pain and myalgia, headaches, heart palpitations, and vaginal dryness) shown in women with menopause, and a menopausal score is obtained by multiplying the score of each item by a weighted value and adding up all the scores.

TABLE 2

| Comparative Example 1 | Comparative Example 2 | Comparative Example 3 | Comparative Example 4 | Example 1 | Example 2 |
|---|---|---|---|---|---|
| 93.3 | 86.2 | 89.3 | 88.7 | 75.7 | 76.8 |

*lower total Kupperman index means more improvement in the symptoms

As shown in Table 2 above, it was confirmed that the composition of Example 1 including the mixture of the Puerariae Flos extract and the Citri Fructus Aurantii extract and the composition of Example 2 including the Puerariae Flos extract and the Citri Pericarpium extract exhibited a more excellent effect of alleviating menopausal symptoms compared to when treated with each extract alone.

Preparation Example 3

Preparation of Tablets

TABLE 3

| Raw material name | Preparation Example 3-1 | Preparation Example 3-2 |
|---|---|---|
| Puerariae Flos extract | 10 | 10 |
| Citri Fructus Aurantii extract | 10 | — |
| Citri Pericarpium extract | — | 10 |
| Crystalline cellulose | 76.5 | 76.5 |
| Silicon dioxide | 1 | 1 |
| Magnesium stearate | 1 | 1 |
| hydroxypropylmethylcellulose | 0.5 | 0.5 |

What is claimed is:
1. A method of preventing or alleviating osteoporosis, the method comprising administering an effective amount of a composition to an individual, comprising:

a Puerariae Flos extract; and an extract of one or more selected from the group consisting of Citri Fructus Aurantii and Citri Pericarpium.

2. The method of claim 1, wherein the composition comprises 1 to 100 parts by weight of the extract of one or more selected from the group consisting of Citri Fructus Aurantii and Citri Pericarpium with respect to 10 parts by weight of the Puerariae Flos extract.

3. The method of claim 1, wherein a total amount of the extracts in the composition is 0.01 wt % or more with respect to a total weight of the composition.

4. The method of claim 1, wherein a total amount of the extracts in the composition is 10 wt % to 30 wt % with respect to a total weight of the composition.

5. A method of treating osteoporosis, the method comprising administering a pharmaceutically effective amount of a composition to an individual, comprising:

a Puerariae Flos extract; and an extract of one or more selected from the group consisting of Citri Fructus Aurantii and Citri Pericarpium.

6. The method of claim 5, wherein the composition comprises 1 to 100 parts by weight of the extract of one or more selected from the group consisting of Citri Fructus Aurantii and Citri Pericarpium with respect to 10 parts by weight of the Puerariae Flos extract.

7. The method of claim 5, wherein a total amount of the extracts in the composition is 0.01 wt % or more with respect to a total weight of the composition.

8. The method of claim 5, wherein a total amount of the extracts in the composition is 10 wt % to 30 wt % with respect to a total weight of the composition.

* * * * *